United States Patent
Flanagan et al.

(10) Patent No.: US 10,559,187 B2
(45) Date of Patent: Feb. 11, 2020

(54) MOISTURE DETECTION SYSTEM

(71) Applicant: Hill-Rom Services, Inc., Batesville, IN (US)

(72) Inventors: Joseph Flanagan, Aurora, IN (US); Christopher D. Newport, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 709 days.

(21) Appl. No.: 14/446,632

(22) Filed: Jul. 30, 2014

(65) Prior Publication Data
US 2014/0340230 A1 Nov. 20, 2014

Related U.S. Application Data

(63) Continuation of application No. 13/185,751, filed on Jul. 19, 2011, now Pat. No. 8,826,473.

(51) Int. Cl.
*A47B 71/00* (2006.01)
*G08B 21/20* (2006.01)
(Continued)

(52) U.S. Cl.
CPC .......... *G08B 21/20* (2013.01); *A61G 7/057* (2013.01); *A61G 7/05784* (2016.11);
(Continued)

(58) Field of Classification Search
CPC .... G08B 21/20; G08B 21/22; A61G 7/05784; A61G 7/057; A61G 2203/30;
(Continued)

(56) References Cited

U.S. PATENT DOCUMENTS

| | | |
|---|---|---|
| 1,772,232 A | 8/1930 | Guilder |
| 2,127,538 A | 8/1938 | Seiger |

(Continued)

FOREIGN PATENT DOCUMENTS

| | | |
|---|---|---|
| CA | 2361145 C | 4/2005 |
| CA | 2494896 C | 2/2007 |

(Continued)

OTHER PUBLICATIONS

SenseSoft™ Incontinence by Sensible Solutions, http://www.sensiblesolutions.se/index.php/incontinence-detection, 2012-2013 Sensible Solutions Sweden AB (1 page).

(Continued)

*Primary Examiner* — Nicholas F Polito
*Assistant Examiner* — Morgan J McClure
(74) *Attorney, Agent, or Firm* — Barnes & Thornburg LLP

(57) ABSTRACT

A moisture detection system for use on a hospital bed includes a person support surface comprising a core layer and a ticking layer. The ticking layer has an inner surface facing the core layer and an outer surface. In one embodiment the moisture detection system also includes a moisture detection sheet which has at least one moisture sensor connected thereto. The sheet is configured to be mounted to at least one of A) the core layer, B) external to the outer surface and C) between the ticking layer and the core layer. A controller is in communication with the moisture detection sensor, and with at least one pre-existing pressure sensor. In another embodiment the moisture detection system includes a detection sheet comprising a fabric which is configured to sense moisture, pressure or both. A controller is in communication with the detection sheet.

25 Claims, 6 Drawing Sheets

(51) Int. Cl.
*A61G 7/057* (2006.01)
*A47C 27/08* (2006.01)
*G08B 21/22* (2006.01)
*A61F 13/42* (2006.01)

(52) U.S. Cl.
CPC ..... *A47C 27/083* (2013.01); *A61B 2562/0247* (2013.01); *A61F 13/42* (2013.01); *A61G 2203/30* (2013.01); *A61G 2203/34* (2013.01); *G08B 21/22* (2013.01); *Y10S 5/904* (2013.01); *Y10S 5/905* (2013.01); *Y10S 5/94* (2013.01)

(58) Field of Classification Search
CPC ..... A61G 2203/34; Y10S 5/904; Y10S 5/905; Y10S 5/94; A61B 5/6891; A61B 5/6892; A61B 5/1115; A61B 5/202; A61B 5/746; A61B 2562/0247; A61B 2562/029; A61F 13/42; A47C 27/083
See application file for complete search history.

(56) References Cited

U.S. PATENT DOCUMENTS

| | | | |
|---|---|---|---|
| 2,644,050 A | 6/1953 | Seiger | |
| 2,668,202 A | 2/1954 | Kaplan | |
| 2,726,294 A | 12/1955 | Kroening et al. | |
| 2,907,841 A | 10/1959 | Campbell | |
| 3,199,095 A | 8/1965 | Ashida | |
| 3,971,371 A | 7/1976 | Bloom | |
| 4,069,817 A | 1/1978 | Fenole et al. | |
| 4,106,001 A | 8/1978 | Mahoney | |
| 4,163,449 A | 8/1979 | Regal | |
| 4,191,950 A | 3/1980 | Levin et al. | |
| 4,212,295 A | 7/1980 | Snyder | |
| 4,228,426 A | 10/1980 | Roberts | |
| 4,347,503 A | 8/1982 | Uyehara | |
| 4,539,559 A | 9/1985 | Kelly et al. | |
| 4,747,166 A | 5/1988 | Kuntz | |
| 4,965,554 A | 10/1990 | Darling | |
| 5,081,422 A | 1/1992 | Shih | |
| 5,086,291 A | 2/1992 | Schwab, Jr. | |
| 5,137,033 A | 8/1992 | Norton | |
| 5,144,284 A * | 9/1992 | Hammett | A61B 5/1115 |
| | | | 128/886 |
| 5,265,296 A | 11/1993 | Abbas et al. | |
| 5,291,181 A | 3/1994 | DePonte | |
| 5,438,721 A * | 8/1995 | Pahno | A61G 7/0005 |
| | | | 4/480 |
| 5,459,452 A | 10/1995 | DePonte | |
| 5,491,609 A | 2/1996 | Dankman et al. | |
| 5,537,095 A | 7/1996 | Dick et al. | |
| 5,675,854 A | 10/1997 | Zibelin | |
| 5,760,694 A | 6/1998 | Nissim et al. | |
| 5,771,511 A | 6/1998 | Kummer et al. | |
| 5,790,035 A | 8/1998 | Ho | |
| 5,824,883 A | 10/1998 | Park et al. | |
| 5,906,016 A * | 5/1999 | Ferrand | A61G 7/00 |
| | | | 5/600 |
| 5,910,080 A | 6/1999 | Selton | |
| 5,947,943 A | 9/1999 | Lee | |
| 6,028,241 A | 2/2000 | Armstead | |
| 6,047,419 A | 4/2000 | Ferguson | |
| 6,104,311 A | 8/2000 | Lastinger | |
| 6,292,102 B1 | 9/2001 | Smith | |
| 6,340,932 B1 | 1/2002 | Rodgers et al. | |
| 6,341,393 B1 | 1/2002 | Votel | |
| 6,351,215 B2 | 2/2002 | Rodgers et al. | |
| 6,362,737 B1 | 3/2002 | Rodgers et al. | |
| 6,384,728 B1 | 5/2002 | Kanor et al. | |
| 6,544,200 B1 | 4/2003 | Smith et al. | |
| 6,552,661 B1 | 4/2003 | Lastinger et al. | |
| 6,583,722 B2 | 6/2003 | Jeutter et al. | |
| 6,603,403 B2 | 8/2003 | Jeutter et al. | |
| 6,621,410 B1 | 9/2003 | Lastinger et al. | |
| 6,639,517 B1 | 10/2003 | Chapman et al. | |
| 6,774,800 B2 | 8/2004 | Friedman et al. | |
| 6,831,562 B2 | 12/2004 | Rodgers et al. | |
| 6,832,507 B1 | 12/2004 | van de Berg et al. | |
| 6,933,849 B2 | 8/2005 | Sawyer | |
| 6,948,205 B2 | 9/2005 | Van Der Wurf et al. | |
| 6,982,646 B2 | 1/2006 | Rodgers et al. | |
| 7,017,213 B2 | 3/2006 | Chisari | |
| 7,030,731 B2 | 4/2006 | Lastinger et al. | |
| 7,071,830 B2 | 7/2006 | Sahlberg et al. | |
| 7,120,952 B1 | 10/2006 | Bass et al. | |
| 7,176,419 B2 | 2/2007 | Ellis et al. | |
| 7,181,206 B2 | 2/2007 | Pedersen | |
| 7,237,287 B2 | 7/2007 | Weismiller et al. | |
| 7,250,547 B1 | 7/2007 | Hofmeister et al. | |
| 7,253,729 B2 | 8/2007 | Lastinger et al. | |
| 7,274,944 B2 | 9/2007 | Lastinger et al. | |
| 7,302,278 B2 | 11/2007 | Lastinger et al. | |
| 7,305,246 B2 | 12/2007 | Lastinger et al. | |
| 7,308,270 B2 | 12/2007 | Lastinger et al. | |
| 7,331,071 B1 * | 2/2008 | Cherubini | A47C 31/00 |
| | | | 340/573.1 |
| 7,348,930 B2 | 3/2008 | Lastinger et al. | |
| 7,349,701 B2 | 3/2008 | Lastinger et al. | |
| 7,355,090 B2 | 4/2008 | Ales, III et al. | |
| 7,359,675 B2 | 4/2008 | Lastinger et al. | |
| 7,400,860 B2 | 7/2008 | Lastinger et al. | |
| 7,424,298 B2 | 9/2008 | Lastinger et al. | |
| 7,489,252 B2 | 2/2009 | Long et al. | |
| 7,489,282 B2 | 2/2009 | Lastinger et al. | |
| 7,498,478 B2 | 3/2009 | Long et al. | |
| 7,506,390 B2 | 3/2009 | Dixon et al. | |
| 7,520,006 B2 | 4/2009 | Mankedick et al. | |
| 7,551,089 B2 | 6/2009 | Sawyer | |
| 7,568,246 B2 | 8/2009 | Weismiller et al. | |
| 7,586,385 B2 | 9/2009 | Rokhsaz | |
| 7,595,734 B2 | 9/2009 | Long et al. | |
| 7,595,756 B2 | 9/2009 | Lastinger et al. | |
| 7,598,853 B2 | 10/2009 | Becker et al. | |
| 7,598,862 B2 | 10/2009 | Lastinger et al. | |
| 7,599,699 B2 | 10/2009 | Lastinger et al. | |
| 7,616,959 B2 | 11/2009 | Spenik et al. | |
| 7,633,378 B2 | 12/2009 | Rodgers et al. | |
| 7,649,125 B2 | 1/2010 | Ales, III et al. | |
| 7,663,483 B2 | 2/2010 | Spenik et al. | |
| 7,667,600 B2 | 2/2010 | Woodbury et al. | |
| 7,812,731 B2 | 10/2010 | Bunza et al. | |
| 7,822,386 B2 | 10/2010 | Lastinger et al. | |
| 7,834,234 B2 | 11/2010 | Roe et al. | |
| 7,834,235 B2 | 11/2010 | Long et al. | |
| 7,834,765 B2 | 11/2010 | Sawyer | |
| 7,834,766 B2 | 11/2010 | Sawyer | |
| 7,838,720 B2 | 11/2010 | Roe et al. | |
| 7,849,544 B2 | 12/2010 | Flocard et al. | |
| 7,873,319 B2 | 1/2011 | Lastinger et al. | |
| 7,977,529 B2 | 7/2011 | Bergman et al. | |
| 8,009,646 B2 | 8/2011 | Lastinger et al. | |
| 8,073,386 B2 | 12/2011 | Pedersen | |
| 8,081,043 B2 | 12/2011 | Rokhsaz | |
| 8,102,254 B2 | 1/2012 | Becker et al. | |
| 8,104,126 B2 | 1/2012 | Caminade | |
| 8,106,782 B2 | 1/2012 | Fredriksson et al. | |
| 8,111,165 B2 | 2/2012 | Ortega et al. | |
| 8,111,678 B2 | 2/2012 | Lastinger et al. | |
| 8,121,856 B2 | 2/2012 | Huster et al. | |
| 8,181,290 B2 | 5/2012 | Brykalski et al. | |
| 8,191,187 B2 | 6/2012 | Brykalski et al. | |
| 8,196,809 B2 | 6/2012 | Thorstensson | |
| 8,237,572 B2 | 8/2012 | Clement et al. | |
| 8,248,249 B2 | 8/2012 | Clement et al. | |
| 8,270,383 B2 | 9/2012 | Lastinger et al. | |
| 8,279,069 B2 | 10/2012 | Sawyer | |
| 8,319,633 B2 | 11/2012 | Becker et al. | |
| 8,325,695 B2 | 12/2012 | Lastinger et al. | |
| 8,332,975 B2 | 12/2012 | Brykalski et al. | |
| 8,345,651 B2 | 1/2013 | Lastinger et al. | |
| 8,395,014 B2 | 3/2013 | Helmer et al. | |
| 8,428,039 B2 | 4/2013 | Lastinger et al. | |
| 8,428,605 B2 | 4/2013 | Pedersen et al. | |

(56) References Cited

U.S. PATENT DOCUMENTS

| | | |
|---|---|---|
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,525,679 B2 | 9/2013 | Riley et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,826,473 B2 | 9/2014 | Flanagan et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,911,387 B2 * | 12/2014 | Lafleche ............ A61G 7/05761 5/652.1 |
| 8,914,923 B2 | 12/2014 | Smith |
| 8,933,292 B2 | 1/2015 | Abraham et al. |
| 8,962,909 B2 | 2/2015 | Groosman et al. |
| 9,048,819 B2 | 6/2015 | Rokhsaz et al. |
| 9,107,776 B2 | 8/2015 | Bergman et al. |
| 2002/0011932 A1 | 1/2002 | Rodgers et al. |
| 2002/0033757 A1 | 3/2002 | Rodgers et al. |
| 2002/0145526 A1 | 10/2002 | Friedman et al. |
| 2003/0030568 A1 | 2/2003 | Lastinger et al. |
| 2004/0128764 A1 * | 7/2004 | McGrath ............ A47C 21/022 5/499 |
| 2005/0003763 A1 | 1/2005 | Lastinger et al. |
| 2005/0003865 A1 | 1/2005 | Lastinger et al. |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0270351 A1 | 11/2006 | Lastinger et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2007/0283496 A1 * | 12/2007 | Skripps ............ A61G 7/05738 5/654 |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0177327 A1 * | 7/2009 | Turner ................ A47C 21/003 700/275 |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0011502 A1 * | 1/2010 | Brykalski ............ A47C 21/044 5/423 |
| 2010/0043143 A1 | 2/2010 | O'Reagan et al. |
| 2011/0025458 A1 | 2/2011 | Rokhsaz et al. |
| 2011/0025473 A1 | 2/2011 | Rokhsaz et al. |
| 2011/0068939 A1 | 3/2011 | Lachenbruch |
| 2011/0092890 A1 * | 4/2011 | Stryker ............ A61G 7/05792 604/23 |
| 2011/0107514 A1 * | 5/2011 | Brykalski ............ A47C 21/044 5/421 |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2012/0092027 A1 | 4/2012 | Forster |
| 2012/0119912 A1 | 5/2012 | Ortega et al. |
| 2012/0130330 A1 | 5/2012 | Wilson et al. |
| 2012/0165772 A1 | 6/2012 | Groosman et al. |
| 2012/0217311 A1 | 8/2012 | Rokhsaz et al. |
| 2012/0268278 A1 | 10/2012 | Lewis et al. |
| 2013/0019406 A1 | 1/2013 | Riley et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0296808 A1 | 10/2014 | Curran et al. |
| 2014/0358099 A1 | 12/2014 | Durgin et al. |
| 2015/0080819 A1 | 3/2015 | Charna et al. |
| 2015/0080834 A1 | 3/2015 | Mills |
| 2015/0087935 A1 | 3/2015 | Davis et al. |
| 2015/0164375 A1 | 6/2015 | Schindheim et al. |
| 2015/0289670 A1 * | 10/2015 | Mojtabavi ............ A47C 27/001 5/730 |

FOREIGN PATENT DOCUMENTS

| | | |
|---|---|---|
| CN | 102568259 | 7/2012 |
| CN | 102568259 A | 7/2012 |
| CN | 202711437 | 1/2013 |
| CN | 202711437 U | 1/2013 |
| CN | 102985853 | 3/2013 |
| CN | 102985853 A | 3/2013 |
| DE | 4137631 A1 | 5/1992 |
| DE | 69906388 | 2/2004 |
| DE | 69906388 T2 | 2/2004 |
| DE | 69915370 | 3/2005 |
| DE | 69915370 12 | 3/2005 |
| DE | 69917491 | 5/2005 |
| DE | 69917491 T2 | 5/2005 |
| DE | 60016946 | 6/2006 |
| DE | 60016946 T2 | 6/2006 |
| DE | 102007050074 | 4/2009 |
| EP | 0335279 | 10/1989 |
| EP | 1153317 B1 | 3/2003 |
| EP | 1147603 B1 | 3/2004 |
| EP | 1149305 B1 | 5/2004 |
| EP | 1218771 B1 | 12/2004 |
| EP | 1286179 B1 | 11/2005 |
| EP | 1645258 | * 4/2006 |
| EP | 1897278 B1 | 6/2006 |
| EP | 1684615 | 8/2006 |
| EP | 1645258 A1 | 12/2006 |
| EP | 1994650 B1 | 2/2007 |
| EP | 2014267 | 6/2007 |
| EP | 1868553 | 12/2007 |
| EP | 2019659 | 2/2009 |
| EP | 1410353 B1 | 12/2009 |
| EP | 1684615 | 2/2010 |
| EP | 2156222 | 2/2010 |
| EP | 2313044 | 4/2011 |
| EP | 2444039 | 8/2011 |
| EP | 1959900 B1 | 2/2012 |
| EP | 2452183 | 5/2012 |
| EP | 2496197 | 9/2012 |
| EP | 2542200 | 1/2013 |
| EP | 2579069 A2 | 4/2013 |
| EP | 2582341 | 4/2013 |
| EP | 2542200 | 2/2014 |
| EP | 2729107 | 5/2014 |
| EP | 2738748 | 6/2014 |
| EP | 2738748 A1 | 6/2014 |
| EP | 2739254 | 6/2014 |
| EP | 2057615 B1 | 12/2014 |

(56) References Cited

FOREIGN PATENT DOCUMENTS

| | | |
|---|---|---|
| EP | 2156222 | 8/2015 |
| EP | 2496197 | 8/2015 |
| EP | 2019659 | 4/2016 |
| EP | 2582341 | 4/2016 |
| EP | 2739254 | 11/2016 |
| GB | 145859 | 3/1919 |
| GB | 2145859 | 4/1985 |
| GB | 2408204 | 11/2003 |
| WO | WO 89/10110 | 4/1989 |
| WO | WO 94/20002 | 3/1994 |
| WO | WO 00/44091 | 7/2000 |
| WO | WO 01/25817 | 4/2001 |
| WO | WO 02/103645 | 12/2002 |
| WO | WO 2006/108540 | 10/2006 |
| WO | WO 2007/069968 | 6/2007 |
| WO | WO 2008130298 A1 | 10/2008 |
| WO | WO 2010001271 A2 | 1/2010 |
| WO | WO 2010/043368 | 4/2010 |
| WO | 2011117862 A2 | 9/2011 |
| WO | WO 2011/107580 | 9/2011 |
| WO | WO 2011152676 A2 | 12/2011 |
| WO | WO 2012/136157 | 10/2012 |
| WO | WO 2012136157 A1 | 10/2012 |
| WO | WO 2014165041 A2 | 10/2014 |
| WO | WO 2015/137999 | 9/2015 |

OTHER PUBLICATIONS

Ostrovsky, Gene, Mar. 26, 2010, 10:07 a.m., *Incontinence Detector Broadcasts The State of Your Pants*, http:/www.medgadget.com/2010/03/incontinene_detector_sends_broadcasts_the_state-of_your_pants.html (2 pages).

Our Product | Simavita, http://simavita.com/product-sales/our-product/; Dec. 22, 2014 (3 pages).

Wood, Molly, *Bedtime Technology for a Better Night's Sleep*, The New York Times, Dec. 24, 2014 (4 pages).

NITE TRAIN-R; Wet Call Bed-Side Bed Wetting Alarm with Pad, www.Amazon.com, Health & Personal Care.

Textile Moisture Sensor Matrix for Monitoring of Disabled and Bed-Rest Patients publication; Tiago Pereira, Pedro Silva—Dep. Industrial Electronics, University of Minho, Guimarales, Portugal; Helder Cavalho, Miguel Cavalho—Dep. Textile Engineering, University of Minho, Guimarales, Portugal; Acknowledgement to FCT, project PTD/SAU-BEB/68678/2006.

Fabric Selection for Textile Moisture Sensor Design publication; Material Science, Textile and Clothing Technology; Jul. 2012; Inese Parkova, Inese Ziemele, Ausma Vilumsone, Riga Technical University.

Electrical Characterization of A Textile Sensor for Moisture Detection; Final Degree Thesis 15 ECTS, Nov. 2010 Sweden; Thesis No. 1/2011, Biomedical Engineering; Arun Swaminathan, Muhammad Babar Khan; Hogskolan I Boras, Institutionen Ingenjorshogskolan.

European Search Report for EP Application 12177071.3; dated Oct. 31, 2014; Place of search—Munich; Date of completion of the search—Oct. 24, 2014.

European Search Report for EP 12177071.3 dated Nov. 2, 2017; 4 pages.

\* cited by examiner

MOISTURE DETECTION SYSTEM

CROSS REFERENCE TO RELATED APPLICATIONS

This application is a continuation of U.S. patent application Ser. No. 13/185,751 entitled "Moisture Detection System" filed on Jul. 19, 2011, the contents of which are incorporated herein by reference.

BACKGROUND OF THE DISCLOSURE

This disclosure relates to a moisture detection system. More particularly, but not exclusively, one illustrative embodiment relates to a moisture detection and alarming system to be used with a person-support apparatus Circumstances may cause the patient to remain confined to a bed for a prolonged period of time, in many instances, for periods greater than a week. Confinement on a bed for continuous and extended time periods may result in accumulation of excessive moisture due to sweating while in contact with the bed. Bed wetting may also be one of the sources of additional of moisture content between the patient body surface and the bed. Presence of excessive moisture for prolonged periods can be very harmful as the patient is susceptible to diseases like skin erosion, fungal infection, pressure ulcer or bed sores. While various moisture sensing devices have been developed, there is still room for improvement. Thus, a need persists for further contributions in this area of technology.

SUMMARY OF THE DISCLOSURE

The present disclosure includes one or more of the features recited in the appended claims and/or the following features which, alone or in any combination, may comprise patentable subject matter.

One embodiment of the current disclosure of a moisture detection system includes a person-support surface comprising a ticking layer and a core layer. The moisture detection system further comprises a removable moisture detection sheet. At least one moisture sensor is connected to the moisture detection sheet. A controller is in communication with the moisture detection sensor and with at least one pre-existing pressure sensor.

In another embodiment a moisture detection system includes a person support surface comprising a ticking layer and a core layer, and a detection sheet. The detection sheet is comprised of a fabric which is configured to sense at least one of moisture and pressure. The system also includes a controller in communication with the detection sheet.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout.

DESCRIPTION OF SPECIFIC ILLUSTRATIVE EMBODIMENTS

Figure 1:
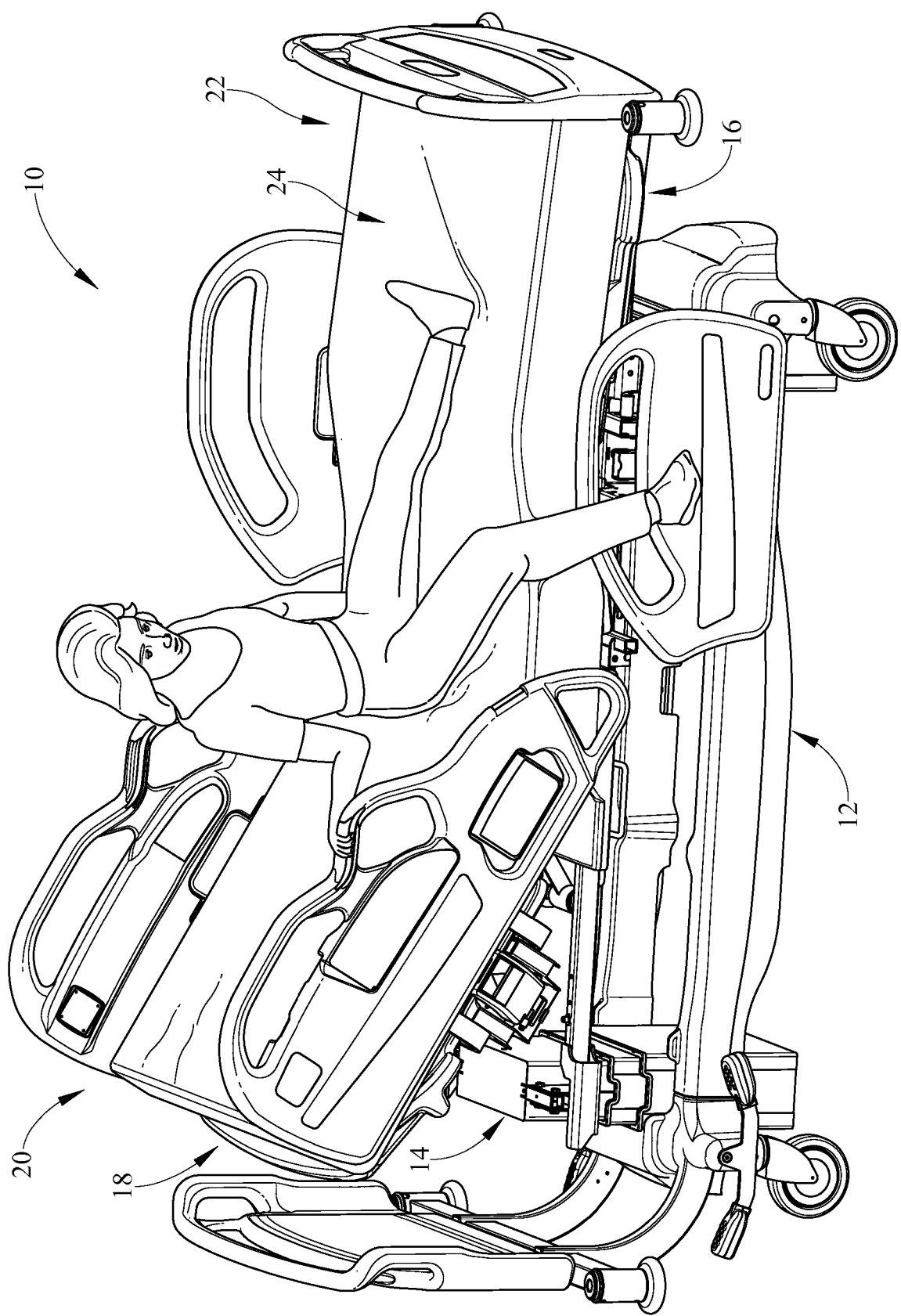
FIG. 1 is a perspective view of a person-support apparatus equipped with a moisture detection system.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

A person-support apparatus 10 according to one illustrative embodiment of the current disclosure is shown in FIG. 1. In one embodiment, the person-support apparatus 10 can be a hospital bed. It should be appreciated that the person-support apparatus 10 can also be a hospital stretcher or an operating table. The person-support apparatus 10 can include a lower frame 12 or base 12, a plurality of supports 14 coupled with the lower frame 12, and an upper frame 16 supported on the plurality of supports 14 above the lower frame 12. The person-support apparatus 10 can also include a deck 18 supported on the upper frame 16. The deck 18 of the person-support apparatus 10 can include a head support section 20 supporting head of the person and a foot support section 22 supporting feet of the person. The deck 18 can further support a person support surface 24 or a mattress 24 as shown in FIG. 1.

Figure 2:
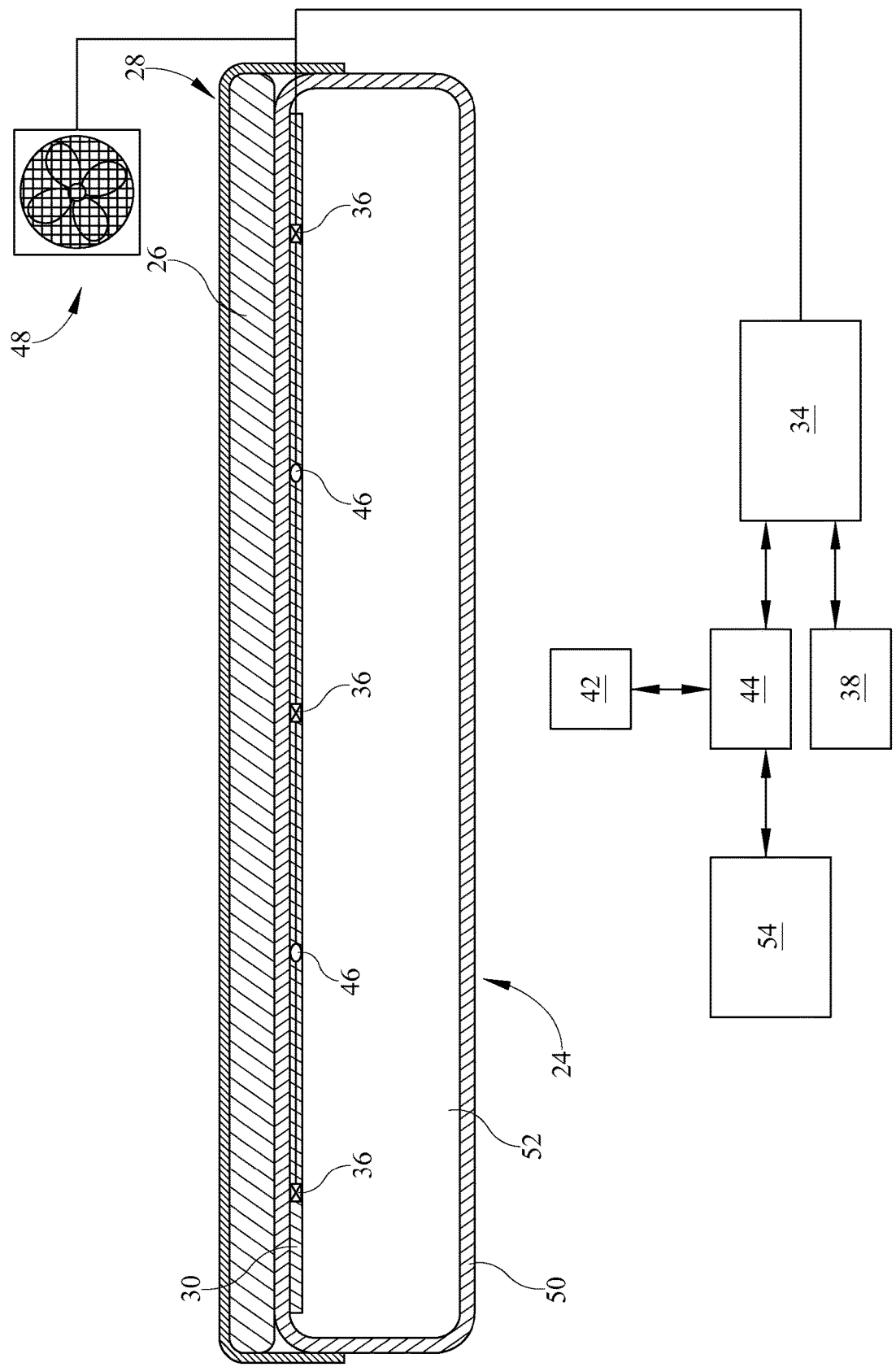
FIG. 2 is a cross-sectional side view of a person-support surface along with an embodiment of the claimed subject matter wherein the moisture detection sheet is located between the ticking layer and the core layer.

The claimed subject matter as shown in FIG. 2 describes a moisture detection system with a person-support surface 24. The person-support surface 24 comprises an outer ticking layer 50 and an inner core layer 52. In one embodiment of the claimed subject matter as shown in FIG. 2, a moisture detection sheet 30 may be included in between the ticking layer 50 and the core layer 52. One skilled in the art would appreciate that the moisture detection sheet 30 may be made of any material, including but not limited to organic and inorganic fabrics, manmade materials and combinations thereof. The moisture detection sheet 30 may be of any size and thickness. The moisture detection sheet 30 has at least one moisture sensor 36 and at least one pressure sensor 46 connected to it. One skilled in the art would appreciate that one or a combination of devices may be used as the moisture sensor 36. These include, but are not limited to capacitive, resistive and thermally conductive sensors. One skilled in the art would appreciate that in one embodiment of the claimed subject matter, fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment fibers of the moisture detection sheet 30 may serve as pressure sensors. The moisture sensor 36 and pressure sensor 46 convey electrical signals to a controller 34. The controller 34 is in communication with a hospital network 44. One skilled in the art would appreciate that the communication between the controller 34 and the hospital network 44 may be through a wired connection or a wireless connection. Wired communication may include communication via the telephone line, Ethernet network, cable and fiber optic cables. Wireless communication may include communication via radio frequency, microwave and infrared (IR) modalities. The hospital network 44 may further be connected to any one or both of a communication station 54 and a nurse call system 42. These connections may also be of a wired or wireless nature as described above. Selective or all of the information from the controller 34 may be transmitted to the communication station 54 and the nurse call system 42. Controller 34 may be communication with an air blower assembly 48 placed external to the outer surface of the ticking layer of the person-support surface 24. The controller 34 provides a signal to the air blower assembly to initiate blowing air. The controller 34 can be electrically coupled to at least one moisture sensor 36 and at least one pressure sensor 46 with the help of wires 40. It should be appreciated that the controller 34 can also be coupled through wireless communication. The controller 34 can be any programmable device configured to receive signals from at least one moisture sensor 36 and send a signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. Although the following elements are not necessary for operation of the claimed subject matter, one skilled in the art would appreciate that several layers may be placed on top of the person-support surface, including, but not limited to a mattress pad 26 and mattress cover 28. One skilled in the art would appreciate that in an embodiment where more than one additional layer has been included with the person-support surface 24, the air blower assembly 48 may be configured to blow air in any combination external to all the layers or between layers.

Figure 3:
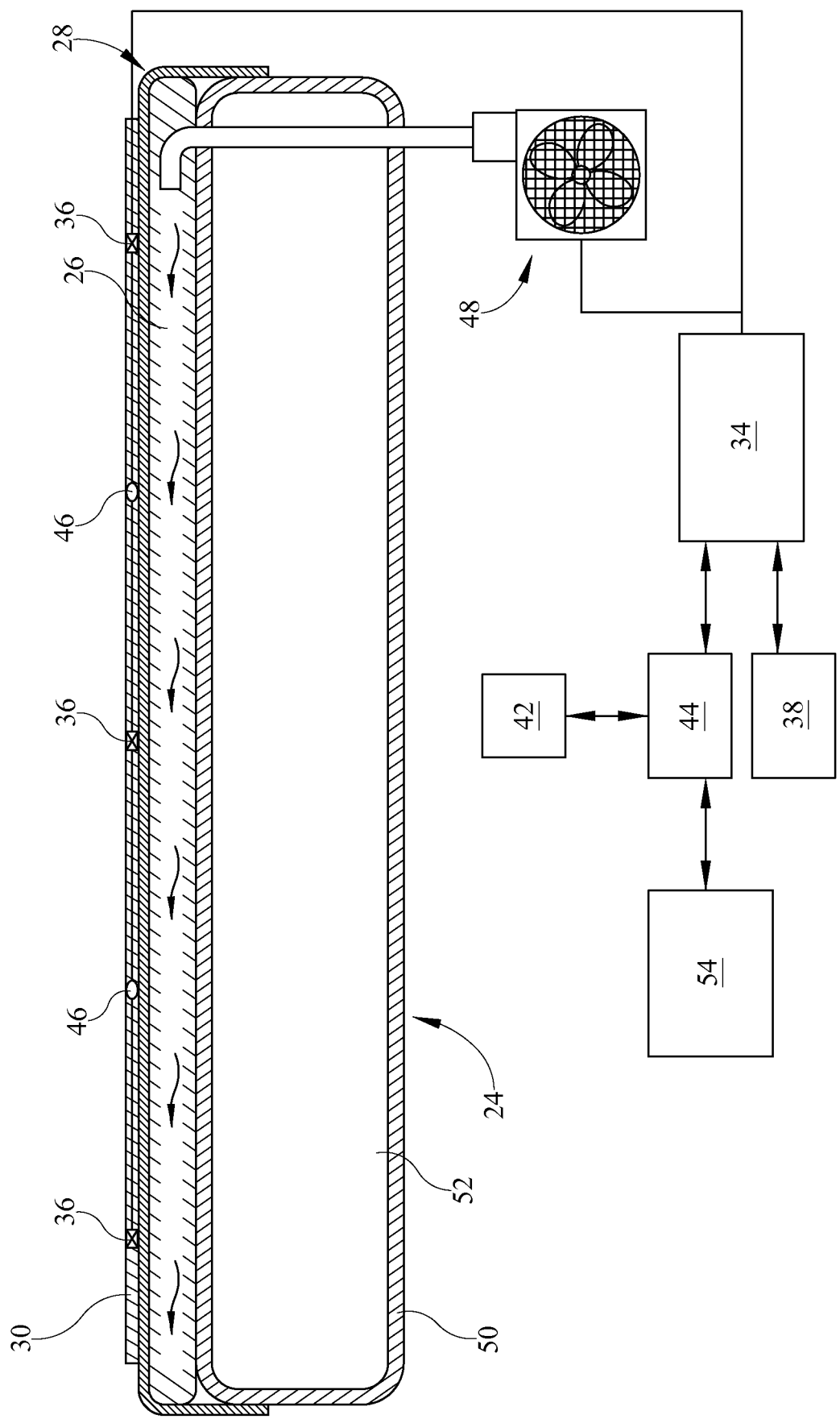
FIG. 3 is a cross-sectional side view of a person-support surface along with an embodiment of the claimed subject matter wherein the moisture detection sheet is located external to the ticking layer.

The claimed subject matter as shown in FIG. 3 describes a moisture detection system with a person-support surface 24. The person-support surface 24 comprises an outer ticking layer 50 and an inner core layer 52. In one embodiment of the claimed subject matter as shown in FIG. 3, a moisture detection sheet 30 may be included external to the person-support surface. Although the following elements are not necessary for operation of the claimed subject matter, one skilled in the art would appreciate that several layers may be placed on top of the person-support surface, including, but not limited to a mattress pad 26 and mattress cover 28. One skilled in the art would appreciate that in an embodiment where more than one additional layer has been included with the person-support surface 24, the moisture detection sheet 30 may be may be placed external to all the layers or between layers. Further, one skilled in the art would appreciate that the moisture detection sheet may simply be placed on top of or between layers or may be integral to any additional layer. Some of the types of connections locating the moisture detection sheet 30 on any other surface may include, but, are not limited to zippered connection, stitched connection, Velcro connection, hooked connection or a buttoned connection. One skilled in the art would appreciate that the moisture detection sheet 30 may be made of any material, including but not limited to organic and inorganic fabrics, manmade materials and combinations thereof. The moisture detection sheet may be of any size and thickness. The moisture detection sheet has at least one moisture sensor 36 and at least one pressure sensor 46 connected to it. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment, fibers of the moisture detection sheet 30 may serve as pressure sensors. The moisture sensor 36 and pressure sensor 46 convey electrical signals to a controller 34. The controller 34 is in communication with a hospital network 44. One skilled in the art would appreciate that the communication between the controller 34 and the hospital network 44 may be through a wired connection or a wireless connection. Wired communication may include communication via the telephone line, Ethernet network, cable and fiber optic cables. Wireless communication may include communication via radio frequency, microwave and infrared (IR) modalities. The hospital network 44 may further be connected to any one or both of a communication station 54 and a nurse call system 42. These connections may also be of a wired or wireless nature as described above. Selective or all of the information from the controller 34 may be transmitted to the communication station 54 and the nurse call system 42. Controller 34 may be in communication with an air blower assembly 48 placed external to the outer surface of the ticking layer of the person-support surface 24. The controller 34 provides a signal to the air blower assembly 48 to initiate blowing air. The controller 34 can be electrically coupled to at least one moisture sensor 36 and at least one pressure sensor 46 with the help of wires 40. It should be appreciated that the controller 34 can also be coupled through wireless communication. The controller 34 can be any programmable device configured to receive signals from at least one moisture sensor 36 and send the signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. One skilled in the art would appreciate that in an embodiment where more than one additional layer has been included with the person-support surface 24, the air blower assembly 48 may be configured to blow air in any combination external to all the layers or between layers.

Figure 4:
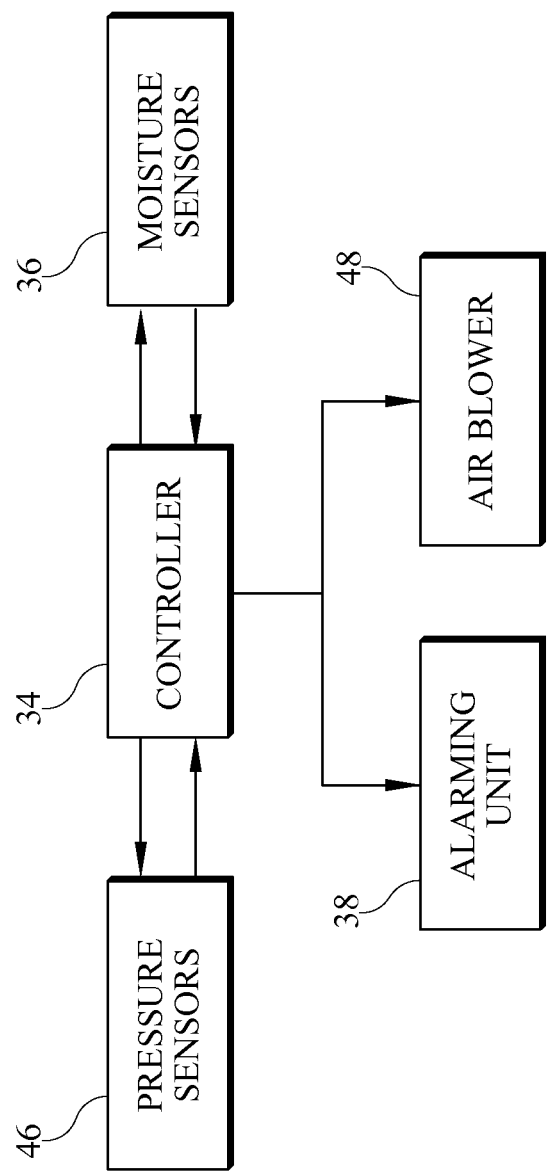
FIG. 4 is a block diagram showing various components and connection of the moisture detection system.

The claimed subject matter as shown in FIG. 4 shows the connections between some of the electro-mechanical, sensing and control elements. The controller 34 is connected to at least one moisture sensor 36 and may further be connected to at least one pressure sensor 46. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. Further, one skilled in the art would appreciate that any one or a combination of devices may be used as the pressure sensor 46. These include, but are not limited to piezoresistive, strain gauge, capacitive, electromagnetic, piezoelectric, optical, potentiometric, resonant, thermal and ionization sensors. One skilled in the art would appreciate that in one embodiment fibers of the moisture detection sheet 30 may serve as pressure sensors. In one embodiment, the pressure sensor 46 may be connected to the moisture detection sheet 30. In another embodiment, the pressure sensor 46 may be mounted on any part of the person-support apparatus 10, person-support surface 24 or any additional layers that may be placed on top of the person-support surface 24. The controller 34 can be any programmable device configured to send a signal to an alarming unit 38. The alarming unit 38 can be at least one of an audio alarm, video alarm, vibration alarm or any other mode. It should also be appreciated that the alarming unit 38 can also include a pre-alarming feature. The pre-alarming feature can activate the alarming unit 38 if the moisture content crosses a second predefined range. Although not shown in FIG. 4, in one embodiment of the claimed subject matter, the controller 34 may be further connected to a hospital network 44, which may in turn be connected to at least one of a nurse call system 42 and a communication station 54. Although not shown in FIG. 4, in another embodiment of the claimed subject matter, the alarming unit 38 may be connected to the hospital network 44. Controller 34 as shown in FIG. 4 is in communication with an air blower assembly 48. Controller 34 provides a signal to the air blower assembly 48 to initiate blowing air. In one embodiment of the claimed subject matter, the air blower assembly 48 may include a timing mechanism which may shut off the air blower assembly 48 automatically after a predetermined period of time. In another embodiment of the claimed subject matter as shown in FIG. 4, the controller 34 may provide a signal to the air blower assembly 48 to stop blowing air. In yet another embodiment, the air blower assembly 48 may include a variety of preprogrammed regimes to blow air at a variety of speeds. In yet another embodiment, although not shown in FIG. 4, the air blower assembly 48 may include a heater element to heat the air.

Figure 5:
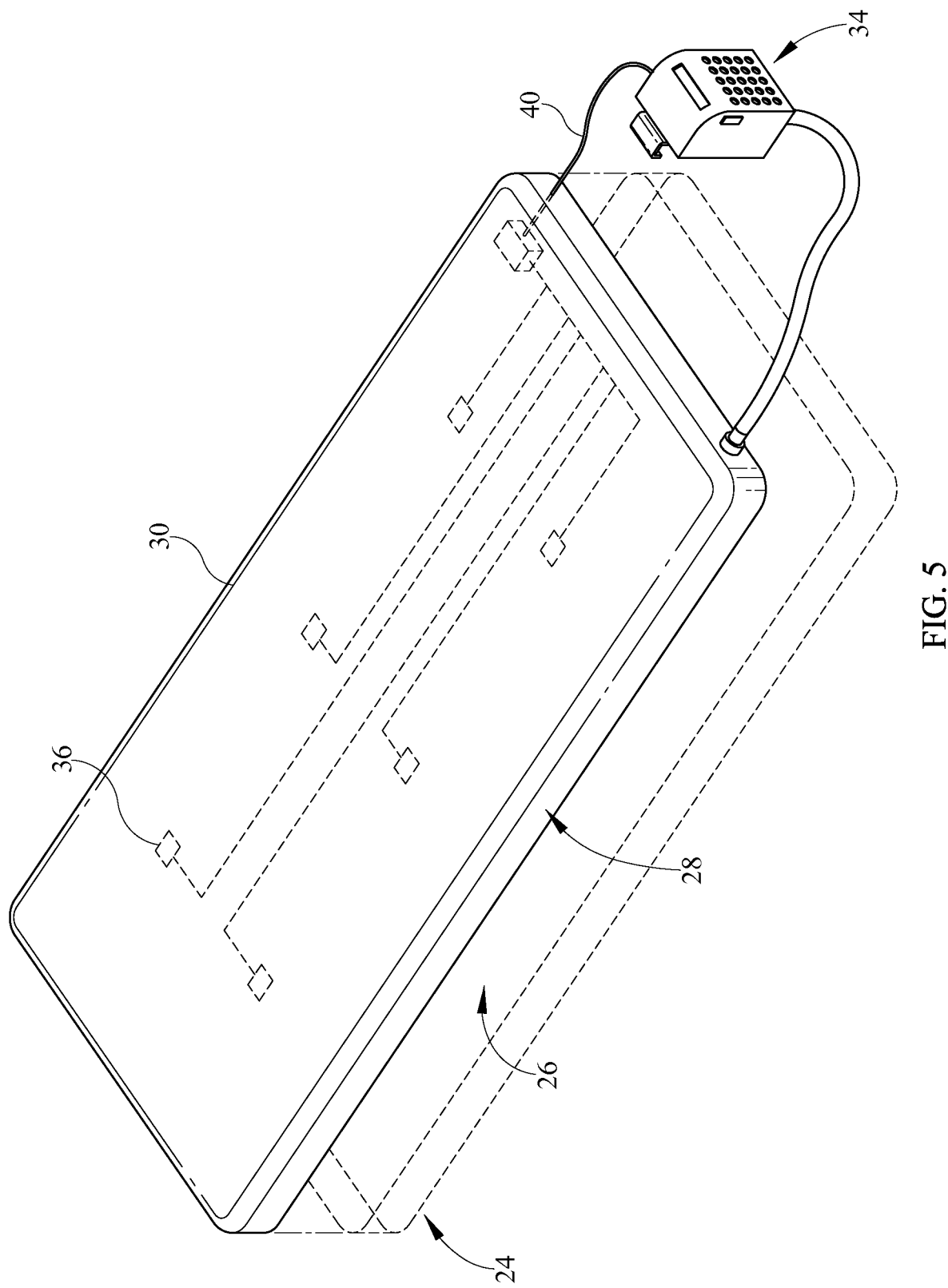
FIG. 5 is a perspective view of the person support surface along with the moisture detection system.

The claimed subject matter as shown in FIG. 5 shows a moisture detection sheet 30 configured to mount on top of a mattress cover 28. One skilled in the art would appreciate that the moisture detection sheet 30 may be placed between any of the layers added on top of the person-support surface 24 or may be placed between the ticking layer 50 and core layer 52 of the patient support surface 24. The moisture detection sheet 30 has at least one moisture sensor 36 connected to it. One skilled in the art would appreciate that one or a combination of devices may be used as the moisture sensor 36. These include, but are not limited to capacitive, resistive and thermally conductive sensors. One skilled in the art would appreciate that in one embodiment fibers of the moisture detection sheet 30 may serve as moisture sensors. A controller 34 can be electrically coupled to at least one moisture sensor 36 with the help of wires 40. It should be appreciated that the controller 34 can also be coupled through wireless communication. The controller 34 can be any programmable device configured to receive signals from at least one moisture sensor 36. In the embodiment shown in FIG. 5, an air blower assembly 48 is integral to the controller 34. The air blower assembly blows air between the mattress cover and the mattress pad as shown in FIG. 5. In another embodiment the air blower assembly may blow air between any of the layers added on top of the person-support surface 24 or between the ticking layer 50 and core layer 52 of the patient support surface 24. Although not shown in FIG. 5, at least one pressure sensor embedded in or connected to any portion of the person-support apparatus 10 provides a signal to the controller 34. In one embodiment of the claimed subject matter shown in FIG. 5, integral to the controller 34 is an alarming unit 38. The alarming unit 38 can be at least one of an audio alarm, video alarm, vibration alarm or any other mode. It should also be appreciated that the alarming unit 38 can also include a pre-alarming feature. In another embodiment, the alarming unit 38 may be a separate system connected to the controller 34.

Figure 6:
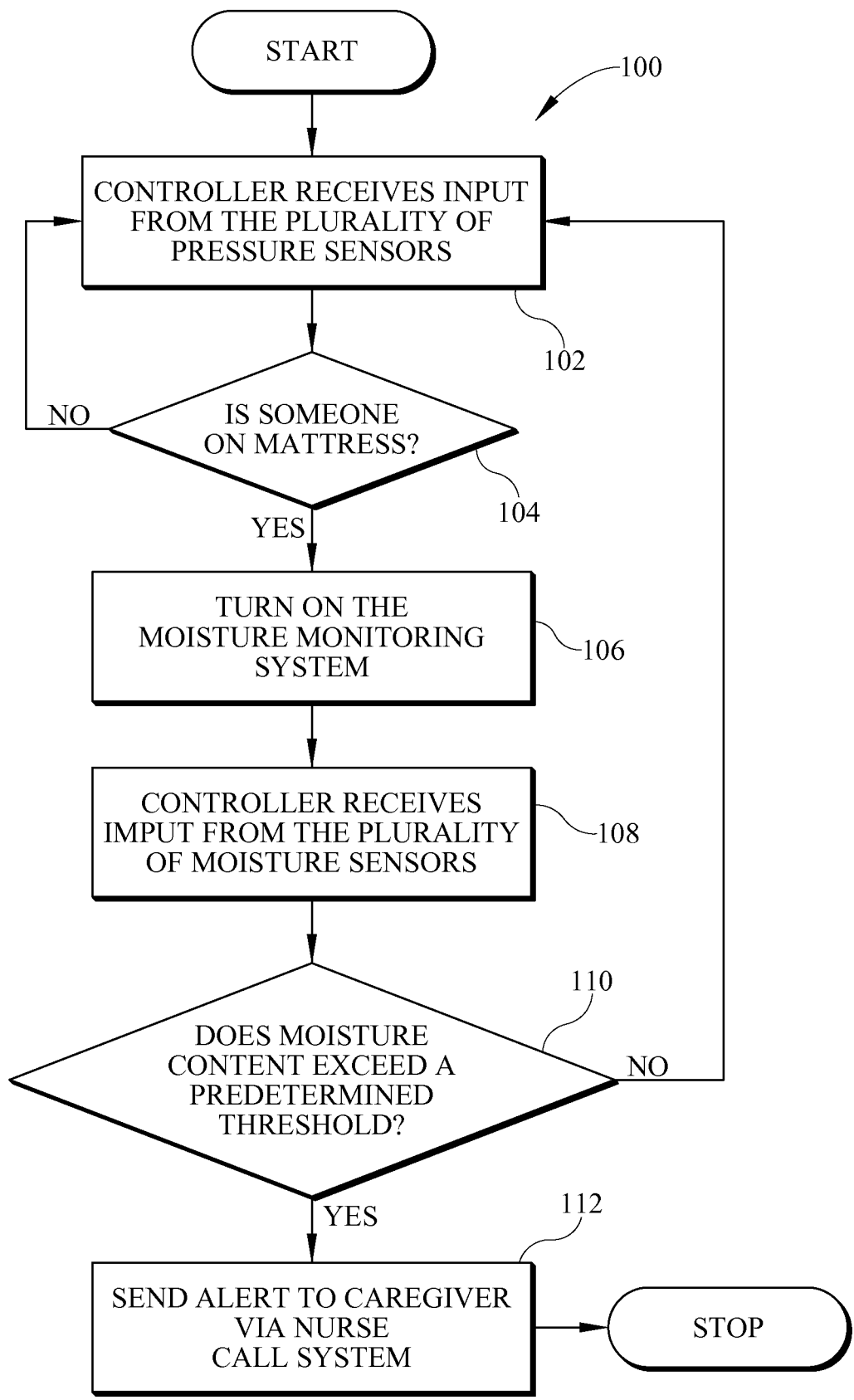
FIG. 6 is a flowchart showing various steps involved in the operation of the moisture detection system.

The claimed subject matter as shown in FIG. 6 shows the operation of one embodiment of the claimed subject matter via a flowchart 100. At step 102, the controller 34 can be configured to receive input from at least one pressure sensor 46. At step 104, the controller 34 can determine the presence of the person on the person-support apparatus 10 by comparing the signal received from the at least one pressure sensor 46 against a predetermined value. If the input from the at least one pressure sensor 46 is above a predetermined value, the controller will activate at least one moisture sensor 36 at step 106. At step 108, controller 34 can be configured to receive input from at least one moisture sensors 36. At step 110 the controller 34 compares the signal received from at least one moisture sensor with a predetermined range of values. At step 112, if the moisture content is more than the predefined range then the controller 34 can send an alert to the alarming unit 38. In another embodiment, at step 112 if the moisture content is more than the predefined range, then the controller sends a signal to the hospital network 44. Although not shown in the FIG. 6, comparison of signals from at least one pressure sensor against another predetermined value may be allow for an alert for a potential patient bed fall. In this case, the controller 34 can send an alert to the alarming unit 38 or the hospital network 44.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless need not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed.

Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A moisture detection system for use on a hospital bed, the moisture detection system comprising:
   a mattress comprising a ticking layer and a core layer, the ticking layer comprising an inner surface and an outer surface, the inner surface facing the core layer;
   a moisture detection sheet configured to be mounted external to the outer surface of the mattress, the moisture detection sheet being a generally planar, unitary sheet covering substantially an entirety of an upper surface of the mattress;
   a plurality of moisture sensors connected to the moisture detection sheet and configured to detect bed wetting of a person atop the moisture detection sheet;
   a plurality of pressure sensors connected to the moisture detection sheet such that the moisture sensors and the pressure sensors are arranged alternately from a first end of the moisture detection sheet to a second end of the moisture detection sheet, wherein the plurality of moisture sensors and the plurality of pressure sensors are arranged in two longitudinal rows spaced from a central region of the moisture detection sheet such that about one third of the moisture detection sheet in a longitudinal direction occupies a space between the two rows with the remainder of the moisture detection sheet being devoid of any of the plurality of moisture sensors and the plurality of pressure sensors;
   a controller in communication with the plurality of moisture detection sensors and in communication with the plurality of pressure sensors, wherein the controller is configured to determine the presence of a person on the hospital bed based on signals received from at least one pressure sensor of the plurality of pressure sensors and, if the person is present on the hospital bed, to turn on moisture monitoring by the plurality of moisture sensors;
   an alarm unit, wherein the controller is configured to trigger the alarm unit in response to one or more of the moisture sensors of the plurality of moisture sensors indicating moisture from bed wetting exceeding a predefined moisture threshold.

2. The moisture detection system of claim 1 wherein the controller is configured to trigger the alarm unit in response to one or more of the pressure sensors of the plurality of pressure sensors indicating pressure exceeding a predetermined pressure threshold.

3. The moisture detection system of claim 1 wherein the controller determines the presence of the person in response to one or more of the pressure sensors of the plurality of pressure sensors indicating pressure exceeding a predetermined pressure threshold.

4. The moisture detection system of claim 3 wherein the controller is configured to trigger the alarm unit in response to one or more of the moisture sensors of the plurality of moisture sensors A) having been activated and B) indicating moisture exceeding a predefined moisture threshold.

5. The moisture detection system of claim 1 wherein the alarm unit provides at least one of an audible sound, a light signal, and vibration in response to having been triggered.

6. The moisture detection system of claim 1 comprising a blower configured to blow air external to and along the outer surface in response to one or more of the moisture sensors of the plurality of moisture sensors indicating moisture exceeding a predefined moisture threshold.

7. The moisture detection system of claim 6 wherein the blower automatically discontinues blowing air after a predetermined period of time.

8. The moisture detection system of claim 6 including a heater for heating the air.

9. The moisture detection system of claim 1 comprising a blower configured to blow air between the ticking layer and the core layer in response to one or more of the moisture sensors of the plurality of moisture sensors indicating moisture exceeding a predefined moisture threshold.

10. The moisture detection system of claim 9 wherein the blower automatically discontinues blowing air after a predetermined period of time.

11. The moisture detection system of claim 9 including a heater for heating the air.

12. The moisture detection system of claim 1, wherein at least one of the moisture sensors of the plurality of moisture sensors comprises a resistive sensor.

13. The moisture detection system of claim 1, wherein at least one of the moisture sensors of the plurality of moisture sensors comprises a capacitive sensor.

14. The moisture detection system of claim 1, wherein at least one of the moisture sensors of the plurality of moisture sensors comprises a thermally conductive sensor.

15. The moisture detection system of claim 1, wherein at least one of the pressure sensors of the plurality of pressure sensors comprises a piezoresistive sensor.

16. The moisture detection system of claim 1, wherein at least one of the pressure sensors of the plurality of pressure sensors comprises a strain gauge sensor.

17. The moisture detection system of claim 1, wherein at least one of the pressure sensors of the plurality of pressure sensors comprises a capacitive sensor.

18. The moisture detection system of claim 1, wherein at least one of the pressure sensors of the plurality of pressure sensors comprises an electromagnetic sensor.

19. The moisture detection system of claim 1, wherein at least one of the pressure sensors of the plurality of pressure sensors comprises a piezoelectric sensor.

20. The moisture detection system of claim 1, wherein at least one of the pressure sensors of the plurality of pressure sensors comprises an optical sensor.

21. The moisture detection system of claim 1, wherein at least one of the pressure sensors of the plurality of pressure sensors comprises a potentiometric sensor.

22. The moisture detection system of claim 1, wherein at least one of the pressure sensors of the plurality of pressure sensors comprises a resonant sensor.

23. The moisture detection system of claim 1, wherein at least one of the pressure sensors of the plurality of pressure sensors comprises a thermal sensor.

24. The moisture detection system of claim 1, wherein at least one of the pressure sensors of the plurality of pressure sensors comprises an ionization sensor.

25. The moisture detection system of claim 1, wherein the moisture detection sheet is configured to mount on the person-support surface with a zippered connection.

* * * * *